(12) United States Patent
Fogwill et al.

(10) Patent No.: US 10,191,020 B2
(45) Date of Patent: Jan. 29, 2019

(54) FLAME IONIZATION DETECTION BURNER ASSEMBLIES FOR USE IN COMPRESSIBLE FLUID-BASED CHROMATOGRAPHY SYSTEMS

(71) Applicant: Waters Technologies Corporation, Milford, MA (US)

(72) Inventors: Michael O. Fogwill, South Grafton, MA (US); Joseph D. Michienzi, Plainville, MA (US); James P. Murphy, Franklin, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 693 days.

(21) Appl. No.: 14/713,439

(22) Filed: May 15, 2015

(65) Prior Publication Data

US 2015/0330956 A1 Nov. 19, 2015

Related U.S. Application Data

(60) Provisional application No. 61/994,353, filed on May 16, 2014.

(51) Int. Cl.
*G01N 30/68* (2006.01)
*F23D 14/00* (2006.01)
*B01D 15/40* (2006.01)

(52) U.S. Cl.
CPC ............ *G01N 30/68* (2013.01); *F23D 14/00* (2013.01); *B01D 15/40* (2013.01); *F23D 2200/00* (2013.01); *F23D 2206/00* (2013.01)

(58) Field of Classification Search
CPC ............... G01N 30/68; G01N 30/685; G01N 2030/685; F23D 14/00; F23D 2200/00;
(Continued)

(56) References Cited

U.S. PATENT DOCUMENTS 1,434,159 A * 10/1922 Skinner ................. F23D 14/00
431/121
1,962,113 A * 6/1934 Elmore ................. F23D 14/00
431/239
(Continued)

FOREIGN PATENT DOCUMENTS

JP 09138218 A * 5/1997 ........... G01N 27/626
JP 11237339 A * 8/1999 ............. G01N 21/72
(Continued)

OTHER PUBLICATIONS

Hudalla, Christopher J., "A New Separation Tool for a Broad Range of Analytical Challenges: UltraPerformance Convergence Chromatography", Chromatography Today, Dec. 2012, pp. 18-20.
(Continued)

*Primary Examiner* — Gregory Huson
*Assistant Examiner* — Daniel E Namay
(74) *Attorney, Agent, or Firm* — Womble Bond Dickinson (US) LLP; Deborah M. Vernon; Rebecca N. Barnes

(57) ABSTRACT

Burner assemblies are configured to deliver decompressed mobile phase of supercritical fluid chromatography systems to the flame of a flame-based detector while providing for improved optimization of analyte response as well as enhanced flame stability during operation.

12 Claims, 11 Drawing Sheets

(58) Field of Classification Search
CPC ... F23D 2206/00; B01F 15/40; F23N 2041/16
USPC .......................................... 431/4, 5, 12, 353
See application file for complete search history.

(56) References Cited

U.S. PATENT DOCUMENTS

| | | | | |
|---|---|---|---|---|
| 1,995,934 A * | 3/1935 | Mangold | ................ | F23D 14/00 239/416.3 |
| 2,117,968 A * | 5/1938 | Lutherer | ................ | F23D 14/00 431/236 |
| 2,241,583 A * | 5/1941 | Campbell | ............... | F23D 14/00 431/249 |
| 2,260,166 A * | 10/1941 | Cope | ...................... | F23D 11/00 431/189 |
| 2,353,865 A * | 7/1944 | Armstrong | .............. | F23D 14/00 137/584 |
| 2,443,259 A * | 6/1948 | Martin | .................... | F23D 14/00 431/171 |
| 2,497,321 A * | 2/1950 | Pattinson | ............... | F23D 14/00 431/172 |
| 2,861,629 A * | 11/1958 | Dailey, Jr. | ............... | F23D 14/00 431/174 |
| 2,934,410 A * | 4/1960 | Smith | ..................... | F23D 14/00 159/4.02 |
| 3,032,096 A * | 5/1962 | Stoul | ...................... | F23D 14/00 431/13 |
| 3,042,499 A * | 7/1962 | Williams, Sr. | ............ | F01N 1/24 422/183 |
| 3,123,127 A * | 3/1964 | Willott | ................... | F23D 14/00 431/177 |
| 3,169,832 A * | 2/1965 | Gallaway | ............. | G01N 27/626 422/89 |
| 3,230,046 A * | 1/1966 | Beroza | .................. | G01N 30/12 422/54 |
| 3,355,252 A * | 11/1967 | De Bliek | ............... | G01N 31/12 356/315 |
| 3,423,181 A * | 1/1969 | Trone | ..................... | G01N 30/68 422/54 |
| 3,450,504 A * | 6/1969 | Korwin | .................. | C01B 3/382 422/129 |
| 3,451,780 A * | 6/1969 | Wise | .................... | G01N 27/626 422/54 |
| 3,456,934 A * | 7/1969 | Ruch | ..................... | F23D 14/00 432/111 |
| 3,558,057 A * | 1/1971 | Akhmedov | ............. | F23D 14/00 239/214.11 |
| 3,732,070 A * | 5/1973 | Vietorisz | ................ | F23D 14/00 431/352 |
| 3,762,878 A * | 10/1973 | Villalobos | .............. | G01N 1/405 422/54 |
| 3,850,579 A * | 11/1974 | Dubsky | .................. | G01N 30/68 422/54 |
| 3,852,037 A * | 12/1974 | Kolb | ...................... | G01N 30/68 422/54 |
| 3,920,401 A * | 11/1975 | Gatiss | .................... | G01N 30/68 422/54 |
| 4,111,554 A * | 9/1978 | Colin | ..................... | G01N 21/72 356/36 |
| 4,182,740 A * | 1/1980 | Hartmann | ............ | G01N 27/626 422/54 |
| 4,215,090 A * | 7/1980 | Dixon | ................... | G01N 27/626 210/198.2 |
| 4,568,267 A * | 2/1986 | Kendall-Tobias | ...... | F23N 1/022 356/315 |
| 4,617,953 A * | 10/1986 | Kendall-Tobias | ........ | F23N 1/00 137/110 |
| 5,049,508 A * | 9/1991 | Hilscher | ................ | G01N 21/72 422/78 |
| 5,990,798 A * | 11/1999 | Sakai | ...................... | F23N 5/242 340/632 |
| 9,739,755 B2 * | 8/2017 | Terai | ...................... | G01N 30/32 |
| 2005/0178747 A1* | 8/2005 | Shibamoto | ............ | G01N 30/68 219/121.47 |
| 2005/0244980 A1* | 11/2005 | Hering | ................. | G01N 1/2214 436/161 |
| 2006/0191200 A1* | 8/2006 | Maenishi | ............... | B01J 8/0257 48/127.9 |
| 2006/0275174 A1* | 12/2006 | Matsushita | ........... | G01N 30/68 422/54 |
| 2007/0031974 A1* | 2/2007 | Jain | ........................ | G01N 30/30 436/161 |
| 2009/0261245 A1* | 10/2009 | Ochiai | ................. | G01N 30/463 250/288 |
| 2010/0059311 A1* | 3/2010 | Agrawal | .............. | F23M 20/005 181/256 |
| 2011/0239737 A1* | 10/2011 | Thurbide | ............... | G01N 30/68 73/23.41 |
| 2013/0220302 A1* | 8/2013 | Han | ........................ | F23D 14/10 126/39 E |
| 2015/0168360 A1* | 6/2015 | Taneda | ............... | G01N 30/8665 73/1.06 |
| 2015/0301000 A1* | 10/2015 | Fogwill | .................. | G01N 30/68 436/160 |
| 2015/0346167 A1* | 12/2015 | Terai | ...................... | G01N 30/32 73/23.41 |

FOREIGN PATENT DOCUMENTS

| | | | | |
|---|---|---|---|---|
| JP | 11237367 A | * | 8/1999 | .......... G01N 27/626 |
| JP | 2002022661 A | * | 1/2002 | ............ G01N 30/68 |

OTHER PUBLICATIONS

Sivasubramaniam, Varatharajan, "Investigation of Flrpic in PhOLEDs via LC/MS technique", Central European Journal of Chemistry, 2009, pp. 836-845, 7(4).

* cited by examiner

FLAME IONIZATION DETECTION BURNER ASSEMBLIES FOR USE IN COMPRESSIBLE FLUID-BASED CHROMATOGRAPHY SYSTEMS

CROSS-REFERENCE TO RELATED APPLICATIONS

This application claims the benefit of and priority to U.S. Provisional Application No. 61/994,353 entitled "Flame Ionization Detection Burner Assemblies for Use in Compressible Fluid-Based Chromatography Systems" filed May 16, 2014, which is incorporated herein by reference in its entirety.

TECHNICAL FIELD

The present disclosure relates to flame ionization detection burner assemblies and their use in compressible fluid-based chromatography systems.

BACKGROUND

Flame ionization detection (FID) was originally developed for use in conjunction with gas chromatography and is nominally designed to operate at relatively low mobile phase flow rates (i.e., up to around 40 mL/min). However, FID is now also commonly employed in conjunction with compressible fluid-based chromatography, hereinafter referred to as "CFC," in which the mobile phase, typically compressed carbon dioxide, is used. An example of CFC is supercritical fluid chromatography, hereinafter referred to as "SFC," in which carbon dioxide in its supercritical state or near supercritical state is typically used as the mobile phase. When decompressed, the CFC mobile phase achieves much higher flow rates than that of gas chromatography. When interfacing a CFC system to an FID detector, a transfer line connected to the CFC system transports some or all of the mobile phase flow to the detector. Due to the compressed nature of the mobile phase, this transfer line must also function as a flow restrictor (i.e., to maintain system pressure). The compressed mobile phase enters the restrictor as a dense fluid and exits as a decompressed gas. Since the fluid expands as it transitions to a gas, the volumetric flow rate at the outlet of the restrictor is considerable. As a result of this expansion, precise positioning of the end of the restrictor within the FID burner is required to ensure stable flame operation and optimal analyte response.

Conventional restrictors in FID burner assemblies are configured such that the flow stream exits the restrictor and into the burner in a direction substantially parallel to the longitudinal axis of the burner. This configuration can be accomplished by simply cutting the end of the restrictor at an angle perpendicular to its longitudinal axis (i.e., a "square cut" restrictor) and is done for ease of manufacture and to ensure restrictor-to-restrictor reproducibility. However, this restrictor design requires considerable burner length to allow for the mobile phase to fully decompress and slow in linear velocity so as to both maintain a stable flame and achieve an optimal analyte response. Thus, the use of "square cut" restrictors in FID burners results in a narrow window of distance from the flame in which the position of the restrictor must be precisely optimized. In a worst case scenario, the mobile phase flow rate out of the restrictor may be so great that the FID burner may not be long enough for optimal positioning of the restrictor at all. A further complication encountered when using such restrictors is that its position within the FID burner must be re-optimized when any change in restrictor flow rate is experienced, such as when the system pressure is changed (i.e., density programmed separations) while operating a split-flow interface to the FID or when the mobile phase flow rate is changed while employing a full-flow interface (i.e., changing column diameter).

Thus, there exists a need for improved FID burner assemblies that do not require precise positioning and re-positioning of the restrictor in order to optimize analyte response and which provide for enhanced flame stability during operation.

SUMMARY OF THE INVENTION

The present disclosure relates to FID burner assemblies and their use in CFC systems. In general and according to certain embodiments, FID burner assemblies of the present disclosure are configured to deliver a decompressed mobile phase fluid (e.g., $CO_2$) from a CFC system to the flame within the detector while providing for improved optimization of analyte response as well as enhanced flame stability during operation.

In one embodiment, the present disclosure relates to a burner assembly of a flame-based detector. The burner assembly comprises a burner and a restrictor. The burner comprises a burner body having a fluid inlet for receiving combustion gases and a fluid outlet for delivering combustion gases to a flame position. The burner body defines a flow path extending from the fluid inlet to the flame position and having a longitudinal axis. The restrictor comprises a hollow body comprising a first end for receiving at least a portion of a mobile phase flow stream from a chromatography system and a second end for delivering at least a portion of the mobile phase flow stream as a decompressed mobile phase flow stream to the burner. During flame-based detection of one or more constituents of the at least a portion of the mobile phase flow stream (1) at least the second end of the restrictor is inserted into the burner and (2) the second end of the restrictor is adapted to deliver the decompressed mobile phase flow stream to the burner body flow path at an angle substantially non-parallel to the longitudinal axis of the burner.

In another embodiment, the present disclosure relates to a burner assembly of a flame-based detector. The burner assembly comprises a burner and a restrictor. The burner comprises a burner body having a fluid inlet for receiving combustion gases and a fluid outlet for delivering combustion gases to a flame position. The burner body defines a flow path extending from the fluid inlet to the flame position and having a burner longitudinal axis. The restrictor comprises a hollow body comprising a first end for receiving at least a portion of a mobile phase flow stream from a chromatography system and a second end for delivering the at least a portion of the mobile phase flow stream as a decompressed mobile phase flow stream to the burner. The restrictor has a restrictor longitudinal axis. During flame-based detection of one or more constituents of the at least a portion of the mobile phase flow stream (1) at least the second end of the restrictor is located within the burner and (2) the restrictor longitudinal axis is substantially non-parallel to the burner longitudinal axis.

In another embodiment, the present disclosure is directed to a burner assembly of a flame-based detector. The burner assembly comprises a burner and a restrictor. The burner comprises a burner body having a fluid inlet for receiving combustion gases and a fluid outlet for delivering combustion gases to a flame position. The burner body defines a flow path extending from the fluid inlet to the flame position and having a longitudinal axis. The restrictor comprises a hollow body having a first end for receiving at least a portion of a mobile phase flow stream from a chromatography system and a second end for delivering the at least a portion of the mobile phase flow stream as a decompressed mobile phase flow stream to the burner. During flame-based detection of one or more constituents of the at least portion of the mobile phase flow stream (1) at least the second end of the restrictor is positioned within the burner; and (2) the burner is adapted so that the at least a portion of the decompressed mobile phase flow stream travels through the flow path in one or more directions substantially non-parallel to the longitudinal axis.

In another embodiment, the present disclosure is directed to a burner assembly of a flame-based detector. The burner assembly comprises a burner and a restrictor. The burner comprises a burner body having a fluid inlet for receiving combustion gases and a fluid outlet for delivering combustion gases to a flame position. The burner body has a longitudinal axis and further comprises an interior wall surface defining an inner perimeter of the burner body and one or more members extending from the interior wall surface at an angle substantially non-parallel to the longitudinal axis. The restrictor comprises a hollow body having a first end for receiving at least a portion of a mobile phase flow stream from a chromatography system and a second end for delivering the at least a portion of the mobile phase flow stream as a decompressed mobile phase flow stream to the burner. During flame-based detection of one or more constituents of the at least portion of the mobile phase flow stream (1) at least the second end of the restrictor is contained within the burner and (2) the one or more members extending from the interior wall are dimensioned and configured to deflect the decompressed mobile phase flow stream in a direction substantially non-parallel to the longitudinal axis.

In another embodiment, the present disclosure is directed to a method of maintaining a flame in a burner assembly of a flame-based detector. The method comprises at least three steps. The first step of the method comprises providing the burner assembly. The burner assembly comprises a burner and a restrictor. The burner comprises a burner body having a fluid inlet for receiving combustion gases and a fluid outlet for delivering combustion gases to a flame position having a flame. The burner body defines a flow path extending from the fluid inlet to the flame position and having a burner longitudinal axis. The restrictor comprises a restrictor comprising a hollow body comprising a first end for receiving at least a portion of a mobile phase flow stream from a chromatography system and a second end for delivering the at least a portion of the mobile phase flow stream as a decompressed mobile phase flow stream to the burner. The second end of the restrictor is sized and inserted into the inner burner. The second step of the method comprises passing at least a portion of the mobile phase flow stream through the restrictor at a decompressed flow rate of 40 mL/min or greater. The third step of the method comprises delivering at least the portion of the mobile phase flow stream into the burner and to the flame position as the decompressed mobile phase flow stream at a force/velocity insufficient to extinguish the flame.

In another embodiment, the present disclosure is directed to a method of maintaining a flame in a burner assembly of a flame-based detector. The method comprises at least three steps. The first step of the method comprises providing the burner assembly. The burner assembly comprises a burner and a restrictor. The burner comprises a burner body having a fluid inlet for receiving combustion gases and a fluid outlet for delivering combustion gases to a flame position having a flame. The restrictor comprises a restrictor comprising a hollow body comprising a first end for receiving at least a portion of a mobile phase flow stream from a chromatography system and a second end for delivering the at least a portion of the mobile phase flow stream as a decompressed mobile phase flow stream to the burner. The second end of the restrictor sized and inserted into the burner. The second step of the method comprises passing at least the portion of the mobile phase flow stream through the restrictor. The third step of the method comprises delivering at least a portion of the mobile phase flow stream into the burner and to the flame position as the decompressed mobile phase flow stream such that the decompressed mobile phase flow stream flows to the flame along a non-parallel fluid flow path.

In another embodiment, the present disclosure is directed to a method of maintaining a flame in a burner assembly of a flame-based detector. The method comprises at least three steps. The first step of the method comprises providing the burner assembly. The burner assembly comprises a burner and a restrictor. The burner comprises a burner body having a fluid inlet for receiving combustion gases and a fluid outlet for delivering combustion gases to a flame position having a flame. The burner body defines a flow path extending from the fluid inlet to the flame position and having a burner longitudinal axis. The restrictor comprises a restrictor comprising a hollow body comprising a first end for receiving at least a portion of a mobile phase flow stream from a chromatography system and a second end for delivering the at least a portion of the mobile phase flow stream as a decompressed mobile phase flow stream to the burner. The second end of the restrictor is sized and inserted into the inner burner. The second step of the method comprises passing at least a portion of the mobile phase flow stream through the restrictor. The third step of the method comprises delivering at least the portion of the mobile phase flow stream into the burner and to the flame position as the decompressed mobile phase flow stream such that a stable flame is maintained and optimal analyte response is achieved regardless of the distance of the restrictor second end from the flame position.

The above embodiments can include one or more of the following features. In some embodiment, the mobile phase flow stream can comprise carbon dioxide. In some of those embodiments, the second end of the restrictor can be adapted to deliver the decompressed mobile phase flow stream at an angle of at least 25 degrees with respect to the longitudinal axis of the inner burner. The second end of the restrictor in some of the above embodiments can also be adapted to provide radial decompression of the mobile phase. Alternatively, it can also comprise a frit or a pintle. In some embodiments, the restrictor is positioned relative to the burner such that the longitudinal axis of the restrictor is at a 90 degree angle relative to that of the burner. In certain embodiments, the flow path of the burner is tortuous or is packed with glass wool. In other embodiments, the interior wall surface of the burner defines a tortuous path between the second end of the restrictor and the flame. Alternatively or in addition thereto, the members extending from the interior wall surface of these burners can be baffles, porous, and/or tapered.

The embodiments of the present disclosure provide advantages over the prior art based on their unique configurations and performance properties. For example, the "square cut" restrictors of conventional FID burner assemblies require precise positioning (and re-positioning when system pressure is changed) of the restrictor in order to optimize analyte response and to maintain flame stability during operation. In contrast, the burner assemblies of the present disclosure do not require precise positioning and re-positioning of the restrictor in order to optimize analyte response and which provide for enhanced flame stability during operation. For example, in certain embodiments of the present disclosure, optimal analyte response is achieved and flame stability maintained regardless of the where the restrictor is positioned inside the burner.

BRIEF DESCRIPTION OF THE DRAWINGS

The foregoing and other features and advantages provided by the present disclosure will be more fully understood from the following description of exemplary embodiments when read together with the accompanying drawings.

DETAILED DESCRIPTION

Figure 1:
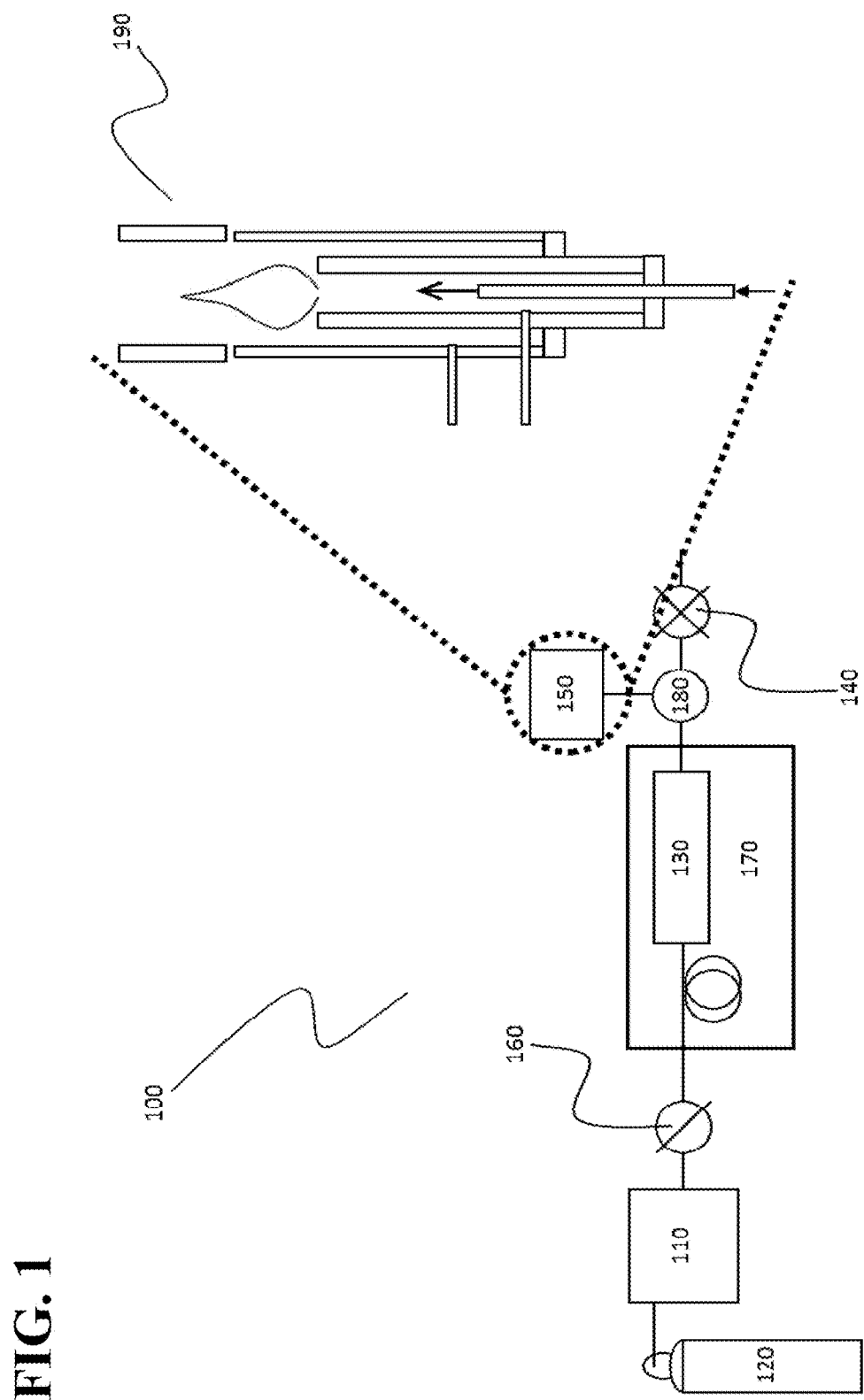
FIG. 1 schematically depicts an exemplary SFC system interfaced with an FID detector, including an enlarged cross-section detail of the FID detector burner assembly.

In various aspects, configurations, and embodiments, the present disclosure provides novel burner assemblies of flame-based detectors, as well as methods of maintaining a flame in such burner assemblies.

As used herein, the phrase "chromatography system" refers to an assembly or array of interconnected components that is used to separate a mixture of compositions. The mixture is dissolved in a fluid mobile phase that carries it through a structure holding a stationary phase. The various constituents of the mixture travel at different speeds through the stationary phase, thereby causing them to separate. An example of such a chromatography system includes, but is not limited to, a compressible fluid-based (CFC) system. An example of a CFC system, includes, but is not limited to, $CO_2$-based a supercritical fluid chromatography (SFC) system, which employs a supercritical fluid or near supercritical fluid as the mobile phase. That is, the mobile phase includes $CO_2$ (and potentially other modifiers) at or near supercritical conditions of the mobile phase for at least some portion of chromatographic process. In some embodiments the $CO_2$ mobile phase does not actually reach the supercritical state, but is highly compressed. The highly compressed $CO_2$ mobile phase provides similar advantages to supercritical $CO_2$ for the purposes of chromatography and is therefore considered to be near supercritical with respect to the performance of SFC.

As used herein, the phrase "flame-based detection" refers to the detection energetic particles (e.g., electrons, photons, etc.) formed during combustion of compounds in a flame. Both organic and inorganic compounds can be ionized and detected. Examples of combustion gases used to produce the flame include, but are not limited to, mixtures of hydrogen and air/oxygen. Nitrogen ($N_2$) is commonly employed as a makeup gas in such mixtures. Examples of such flame-based detection include, but are not limited to, flame ionization detection (FID), flame photometric detection, chemiluminescence nitrogen detection, thermionic detection (e.g., nitrogen-phosphorus detection), and chemiluminescence sulfur detection.

As used herein, the phrase "longitudinal axis" refers to the axis of symmetry that runs lengthwise from the fluid inlet, through the flow path, to the fluid outlet of the burner body or the axis of symmetry that runs lengthwise from the first end, through the hollow body, to the second end of the restrictor.

As used herein, the phrase "decompressed" refers to the phase transition of the supercritical fluid of the mobile phase from a liquid, a supercritical fluid, or a highly compressed gas to a gas.

As used herein, the phrase "substantially non-parallel" refers to the angle at which the mobile phase flow stream decompresses (i.e., the "angle of decompression"), relative to the longitudinal axis of the burner, sufficient to prevent the decompressed mobile phase flow stream from extinguishing the flame at the flame position. Such an angle can be any angle greater than 0° to 180°, relative to the longitudinal axis of the burner. Examples of such angles include, but are not limited to, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 160, 165, 170, and 175, and 180°. In some embodiments, the angle is greater than 22°. In other embodiments, the angle is 45, 67, 90, or 135°.

An example of an SFC system that employs supercritical $CO_2$ as the mobile phase is illustrated in FIG. 1. SFC system 100 includes $CO_2$ pump 110, which pumps $CO_2$ from $CO_2$ source 120 into system 100 at a pressure that maintains the $CO_2$ in a dense state, column 130, back pressure regulator (BPR) 140, and flame ionization detection (FID) detector 150. The $CO_2$ mobile phase flows from $CO_2$ pump 110 to column 130. Injector 160 for injecting mixtures to be separated is located in-line between $CO_2$ pump 110 and column 130. Column 130 is housed in column oven 170, which maintains column 130 at a constant temperature. Column oven 170 also functions to preheat the supercritical $CO_2$ mobile phase and the mixture for separation to the constant temperature of column 130 prior to their entry.

Flow splitter 180 is located in-line between column oven 170 and BPR 140. Flow splitter 180 operates to divert at least a portion of the mobile phase flow, which now contains the separated constituent compounds of the mixture, (i.e., the column effluent), to FID detector 150, where one or more compounds are ionized via combustion in burner assembly 190 of FID 150.

Figure 2:
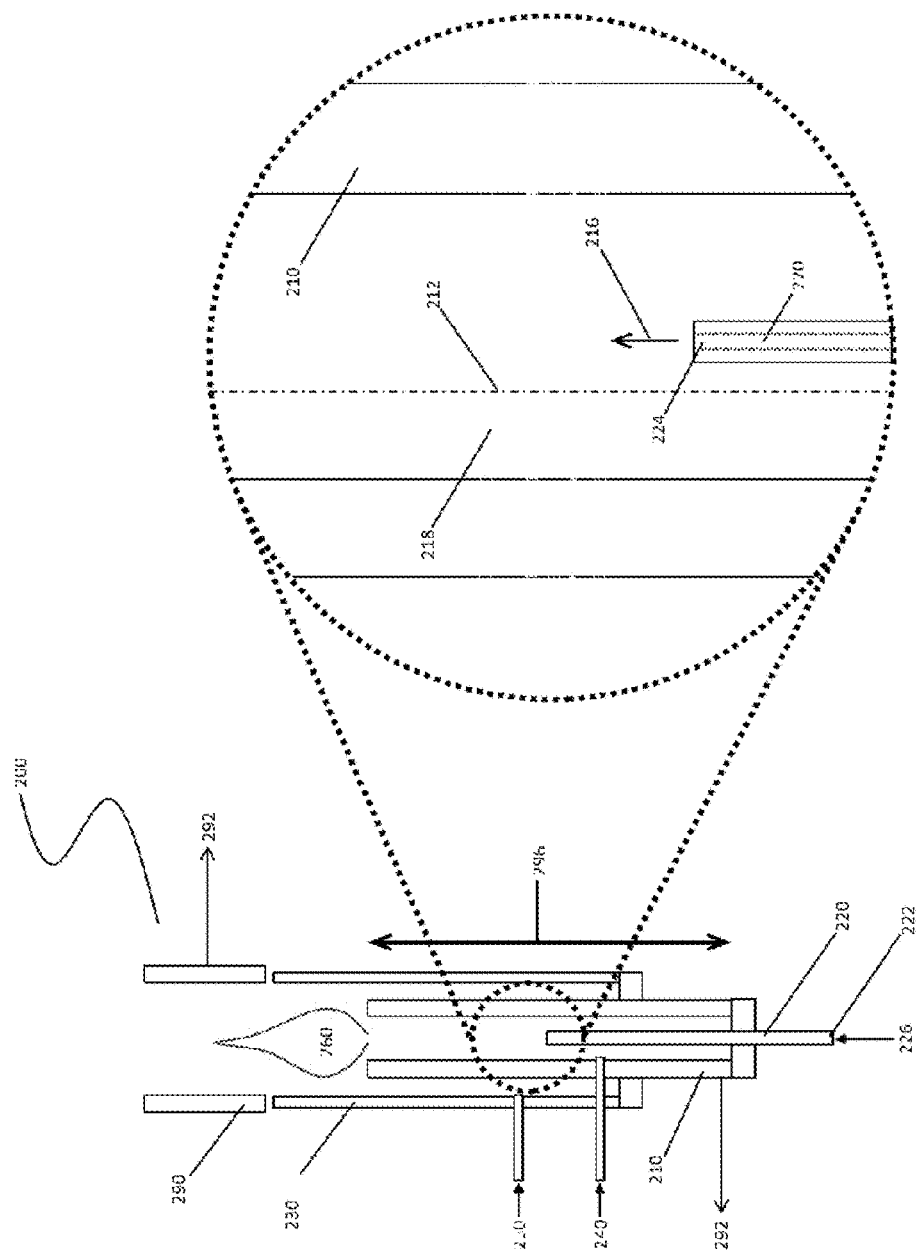
FIG. 2 depicts a cross-section of a burner assembly with a conventional "square cut" restrictor.

As discussed above, one component of an FID detector is the burner assembly. A cross-section of an exemplary burner assembly is illustrated in FIG. 2. Assembly 200 includes burner 210 and restrictor 220, a portion of which located inside burner 210. A portion of burner 210 is, in turn, located inside burner housing 230. Inlets 240 and 250 supply assembly 200 with fuel gas and oxidant gas, respectively, (together, combustion gases), which mix at flame position 260 and are then combusted. The flame produced at position 260 is a "diffusion" flame, the exterior of which is an oxidant-rich region and the interior of which is a fuel gas-rich region. The second end 224 of restrictor 220 can be positioned inside burner 210 at any distance 296 relative to flame position 260. Column effluent 226 is fed to the FID detector, entering restrictor 220 at its first end 222 and exiting at its second end 224 at an angle substantially parallel to the longitudinal axis 212 of burner 210, where it decompresses and travels through flow path 218 of burner 210 to flame position 260, where one or more separated constituent compositions of the mixture are ionized via combustion. The electrons released during ionization are attracted to collector electrode 290, where they induce a current, which is, in turn, fed to electrometer 292.

As can be seen in FIG. 2, the second end 224 of restrictor 220 is "square cut." This geometry results in the mobile phase flow having a mean direction 216 substantially parallel to the longitudinal axis 212 of burner 210 as it exits the second end 224 of restrictor 220 and decompresses into flow path 218. One problem with this restrictor geometry is that re-positioning of the second end 224 of restrictor 220 relative to flame position 260 may be required any time the flow rate of the mobile phase is changed in order to optimize detector response. Another problem is that, depending on the flow rate of the mobile phase, it may not be possible with this restrictor geometry to maintain a stable flame at certain distances 296 (or even regardless of the distance) of the second end 224 from flame position 260.

These problems are solved by the various burner assembly configurations of the present disclosure.

All of the burner assembly configurations of the present disclosure comprises a burner and a restrictor. The burners of these configurations comprise a burner body having a fluid inlet for receiving combustion gases and a fluid outlet for delivering at least a portion of the combustion gases to a flame position. The burner bodies define a flow path extending from the fluid inlet to the flame position and having a longitudinal axis. The restrictors of these configurations comprise a hollow body comprising a first end for receiving at least a portion of a mobile phase flow stream from a chromatography system and a second end for delivering the at least a portion of the mobile phase flow stream as a decompressed mobile phase flow stream to the burner. In all configurations, at least the second end of the restrictor is inserted into the burner during flame-based detection of one or more constituents of the at least a portion of the mobile phase flow stream.

During flame-based detection, the flame-based detector is typically maintained at a temperature above ambient temperature. For example, the flame-based detector can be maintained at a temperature in the range of from about 50 to 500° C. or higher. In certain embodiments, the flame-based detector can be held at a temperature of about 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500° C. during flame-based detection.

Both the burner and the restrictor of the burner assemblies of the present invention can be fabricated from any material capable of withstanding the temperatures at which the flame-based detectors are maintained. These materials also should not "de-gas" or otherwise introduce extraneous carbon containing compounds into the FID flame. Such materials include, but are not limited to metals, ceramics, glass, or polymers. In one embodiment, the burner is fabricated from a metal, such as steel. In one embodiment, the restrictor is fabricated from glass. Furthermore, the restrictor and its second end can be fabricated as separate, optionally disposable/replaceable, pieces that can be fitted together. These two pieces can be fabricated from the same or different materials.

The cross-sectional dimensions of the burner and the restrictor can be any width and shape, with the only conditions being that the width and shape of the restrictor should be such that it can be inserted into the burner and there is space between the inner surface of the burner and the outer surface of the restrictor sufficient to allow combustion gas(es) to move freely towards the flame position. In certain embodiments, the cross-sectional width of the burner can be about 15, 14, 13, 12, 11, 10, 9, 8, 7, 6, 5, 4, 3, 2, 1, 0.762, 0.75, 0.5, 0.457, 0.28, or 0.25 mm. In certain embodiments, the cross-sectional width of the restrictor can be about 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, 0.1, 0.090, 0.080, 0.070, 0.060, 0.050, 0.049, 0.048, 0.047, 0.046, 0.045, 0.044, 0.043, 0.042, 0.041, 0.040, 0.039, 0.038, 0.037, 0.036, 0.035, 0.034, 0.033, 0.032, 0.031, 0.030, 0.029, 0.028, 0.027, 0.026, 0.025, 0.024, 0.023, 0.022, 0.021, 0.020, 0.010, 0.009, 0.008, 0.007, 0.006, 0.005, 0.004, 0.003, 0.002, or 0.001 mm. In certain embodiments, the cross-sectional shape of the burner and/or the restrictor can be a circle, an oval, a square, a rectangle, or a triangle. In a microfluidic embodiment, the cross-sectional shape of the burner can be trapezoidal or "gumdrop" shaped.

The longitudinal dimensions of the burner and the restrictor can be any length and shape. In certain embodiments, the length of the burner can be about 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 mm. In certain embodiments, the length of the restrictor can be about 200, 199, 198, 197, 196, 195, 194, 193, 192, 191, 190, 189, 188, 187, 186, 185, 184, 183, 182, 181, 180, 179, 178, 177, 176, 175, 174, 173, 172, 171, 170, 169, 168, 167, 166, 165, 164, 163, 162, 161, 160, 159, 158, 157, 156, 155, 154, 153, 152, 151, 150, 149, 148, 147, 146, 145, 144, 143, 142, 141, 140, 139, 138, 137, 136, 135, 134, 133, 132, 131, 130, 129, 128, 127, 126, 125, 124, 123, 122, 121, 120, 119, 118, 117, 116, 115, 114, 113, 112, 111, 110, 109, 108, 107, 106, 105, 104, 103, 102, 101, 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, or 10 cm. In certain embodiments, the longitudinal shape of the burner and/or restrictor can be cylindrical or tubular. In other embodiments, the longitudinal shape of the burner and/or restrictor can be cylindrical or tubular, pinched in one or more positions along the length of the burner and/or restrictor, or undulates along the length of the burner and/or restrictor, such that the flow of the mobile phase and/or the combustion gas(es) converge and diverge along the flow path. In one embodiment, the restrictor can be longer than the burner. In another embodiment, the restrictor can be 35 cm long and the burner can be 25 mm long.

In certain embodiments, the combustion gases can be hydrogen, as the fuel gas, in mixture with an oxidant gas, such as oxygen or air. Use of carbon-based gases should be avoided. Nitrogen can be used as a makeup gas. In one embodiment, the combustion gases are hydrogen and air or oxygen, with nitrogen as the makeup gas.

The mobile phase can comprise any supercritical fluid. In certain embodiments, the supercritical fluid can be $CO_2$, $N_2$, Ar, Xe, a chlorofluorocarbon, a fluorocarbon, $N_2O$, $H_2O$, or $SF_6$. The mobile phase can also comprise one or more FID-compatible modifiers. Example of such modifiers include, but are not limited to, formic acid, trifluoroacetic acid, and other highly oxidized carbon-containing compounds.

Figure 10A:
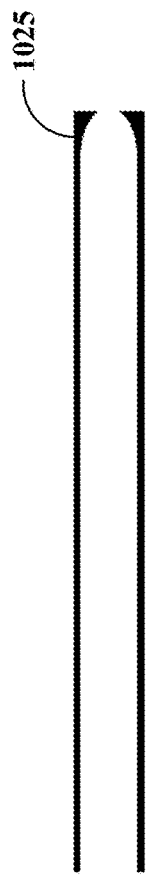
FIG. 10A depicts a cross-section of an integral restrictor according to the present disclosure.
Figure 10B:
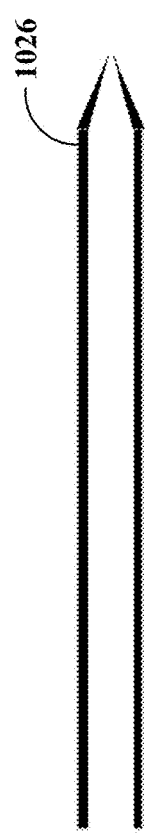
FIG. 10B depicts a cross-section of a tapered restrictor according to the present disclosure.
Figure 10C:
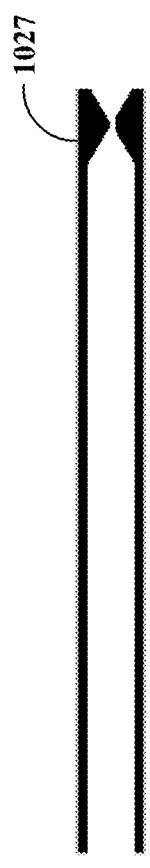
FIG. 10C depicts a cross-section of a converging-diverging restrictor according to the present disclosure.
Figure 10D:
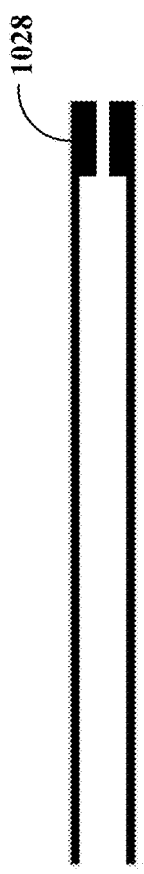
FIG. 10D depicts a cross-section of a linear hybrid restrictor according to the present disclosure.

In one of the above burner assembly configurations, the second end of the restrictor is adapted to deliver the decompressed mobile phase flow stream to the burner body flow path at an angle substantially non-parallel to the longitudinal axis of the burner. This adaptation of the second end of the restrictor can be achieved in any number of ways. For example, the second end can be "angled," i.e., the second end can be cut at an angle less than or greater than perpendicular to the longitudinal axis of the restrictor (90°). The "angle of cut" includes any angle in the range of from greater than 0° to less than 90° and the range of from greater than 90° to less than 180°. Such an angle of cut results in an angle of decompression of the mobile phase flow stream that is substantially non-parallel to the longitudinal axis of the burner. Example of such angles of cut include, but are not limited to, 5, 10, 15, 20, 25, 30, 35, 40, 45, 50, 55, 60, 65, 70, 75, 80, 85, 95, 100, 105, 110, 115, 120, 125, 130, 135, 140, 145, 150, 155, 160, 165, 170, and 175°. In some embodiments, the angle of cut results in an angle of decompression that is greater than 22°. In other embodiments, the angle of cut results in an angle of decompression that is 45, 67, 90, or 135°. Other examples of such adaptations include, but are not limited to, (1) a restrictor where the second end has been roughly cleaved, resulting in a jagged end surface, (2) a restrictor where the opening at the second end is sealed and a second opening is formed by drilling one or more holes into the side of the restrictor (i.e., a "drilled" restrictor), (3) a restrictor fitted with a frit (i.e., a "fritted" restrictor), wherein the top of the frit is optionally sealed, (4) a restrictor fitted with a pintle (i.e., a "pintled" restrictor) (5) an integral restrictor, (6) a restrictor where the second end has been tapered, such that the restrictor flow path dimensions perpendicular to the longitudinal axis of the restrictor decrease as the flow path approaches the second end, i.e., the flow path narrows as it approaches the second end, (7) a converging/diverging restrictor, and (8) a linear hybrid restrictor. Each of restrictor examples (5), (6), (7), and (8) have short decompression zones and are easily plugged. Illustrations of exemplary restrictors (5), (6), (7), and (8) are provided in FIGS. 10A, 10B, 10C, and 10D, respectively. That is, FIG. 10A shows a cross-sectional view of an embodiment of an integral restrictor 1025; FIG. 10B shows a cross-sectional view of an embodiment of a restrictor with a tapered second end 1026; FIG. 10C shows a cross-sectional view of an embodiment of converging/diverging restrictor 1027; and FIG. 10D shows a cross-sectional view of an embodiment of a linear hybrid restrictor 1028.

Figure 3:
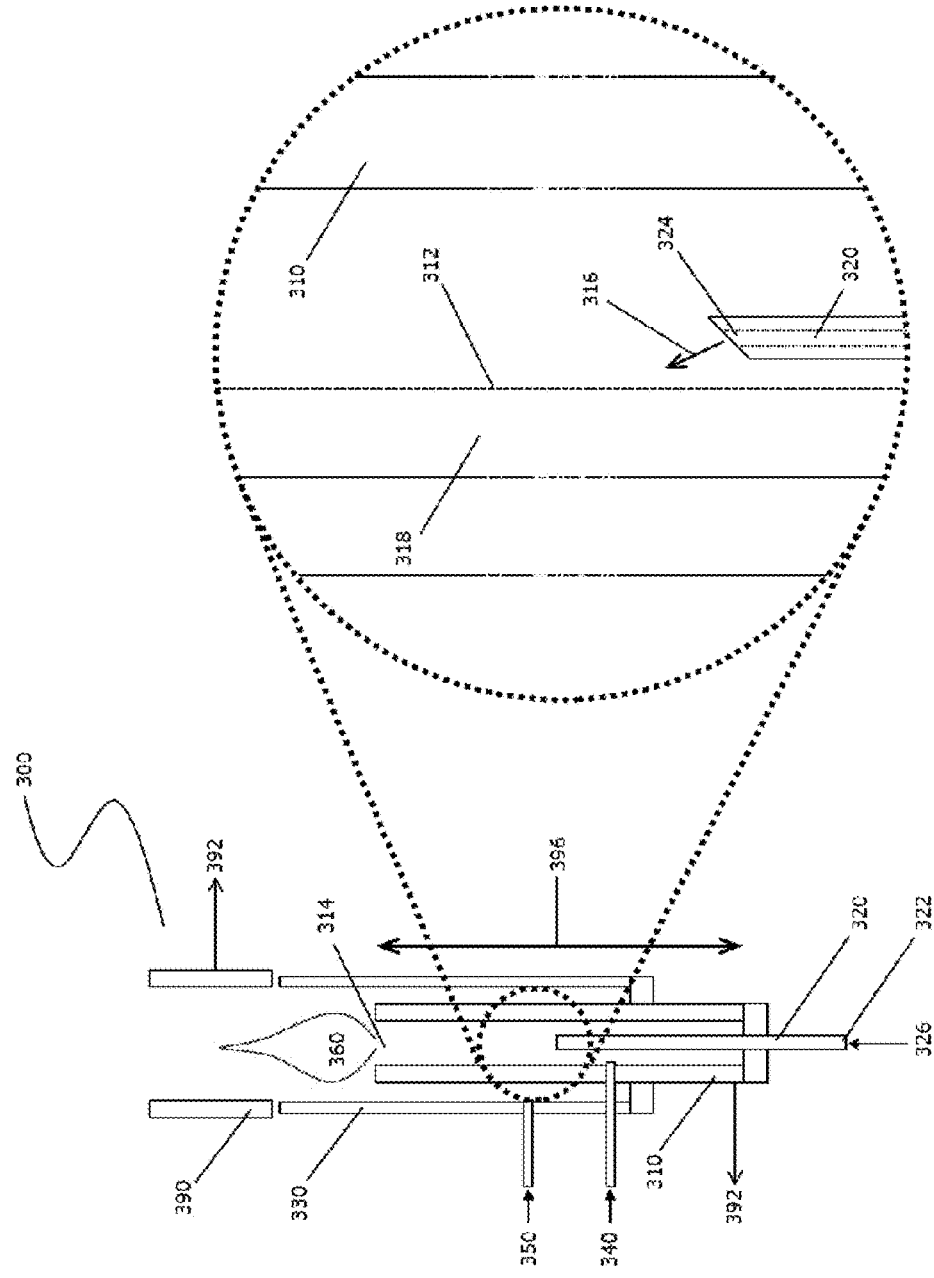
FIG. 3 depicts a cross-section of a burner assembly according to the present disclosure where the restrictor has a tip cut at an angle of less than 90°.

An example of a burner assembly configuration where the second end of the restrictor is angled is illustrated in FIG. 3. Burner assembly 300 comprises a burner 310 and restrictor 320. Burner 310 comprises a burner body having fluid inlets 340 and 350 for receiving combustion gases and a fluid outlet 314 for delivering at least a portion of the combustion gases to flame position 360. Restrictor 320 comprises a first end 322 and a second end 324. Second end 324 of restrictor 320 is located within burner 310. A portion of burner 310 is, in turn, located inside burner housing 330. Second end 324 of restrictor 320 can be positioned inside burner 310 at any distance 396 relative to flame position 360. Column effluent 326 is fed to the FID detector, entering restrictor 320 at its first end 322 and exiting at its second end 324 at an angle 316 substantially non-parallel to the longitudinal axis 312 of burner 310. The mobile phase of the column effluent decompresses and travels through flow path 318 of burner 310 to flame position 360, where one or more separated constituent compositions of the mixture are ionized via combustion. These ions are attracted to collector electrode 390, where they induce a current, which is, in turn, fed to electrometer 392.

Figure 4:
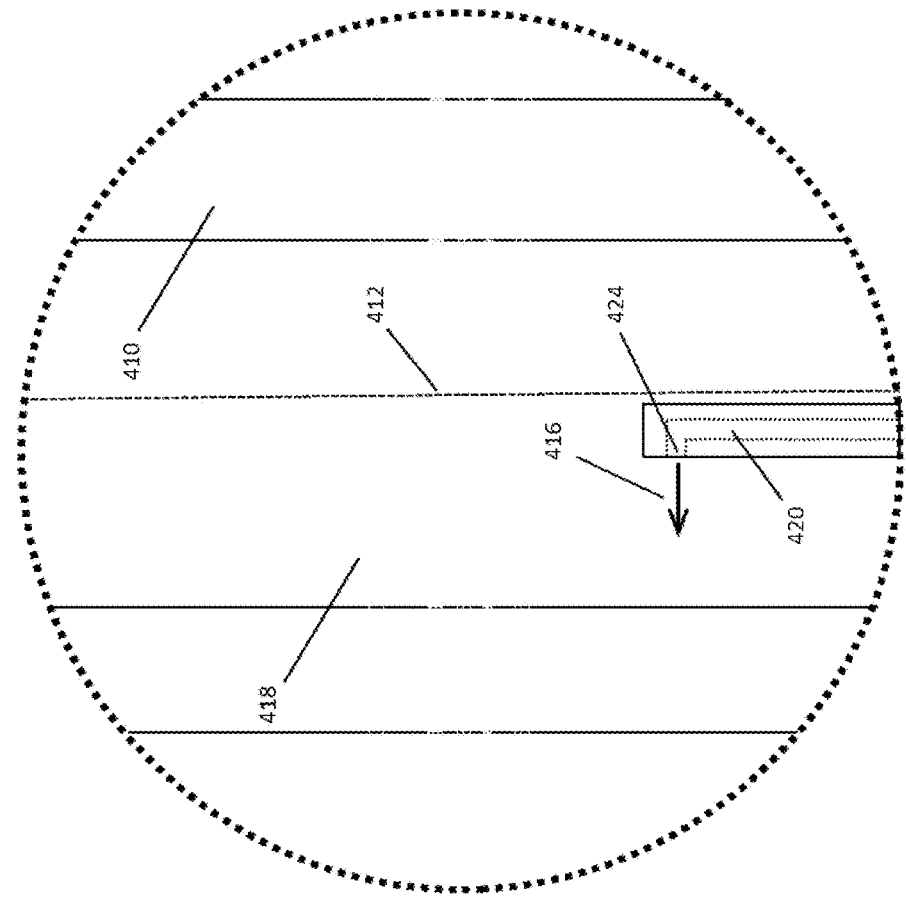
FIG. 4 depicts a cross-section of a portion of a burner assembly according to the present disclosure where the restrictor has a drilled tip.

An example of a burner assembly configuration having a "drilled" restrictor is illustrated in FIG. 4. In this example, the configuration of the burner assembly is identical to that of FIG. 3 except for the adaptation to the second end of the restrictor. Column effluent exits at the second end 424 of restrictor 420 at an angle 416 substantially non-parallel to the longitudinal axis 412 of burner 410. The mobile phase of the column effluent decompresses and travels through flow path 418 of burner 410 to the flame position. "Drilled" restrictors can be fabricated from a conventional "square cut" restrictor by sealing the end of the restrictor, followed by drilling one or more holes into its side until the interior channel of the restrictor is reached. The hole can be drilled using a laser or a mechanical drill. The holes can be drilled at any angle in the range of from greater than 0° to less than 180°, relative to the longitudinal axis of the restrictor. In one embodiment the one or more holes are drilled at an angle of 90°, relative to the longitudinal axis of the restrictor.

Figure 5A:
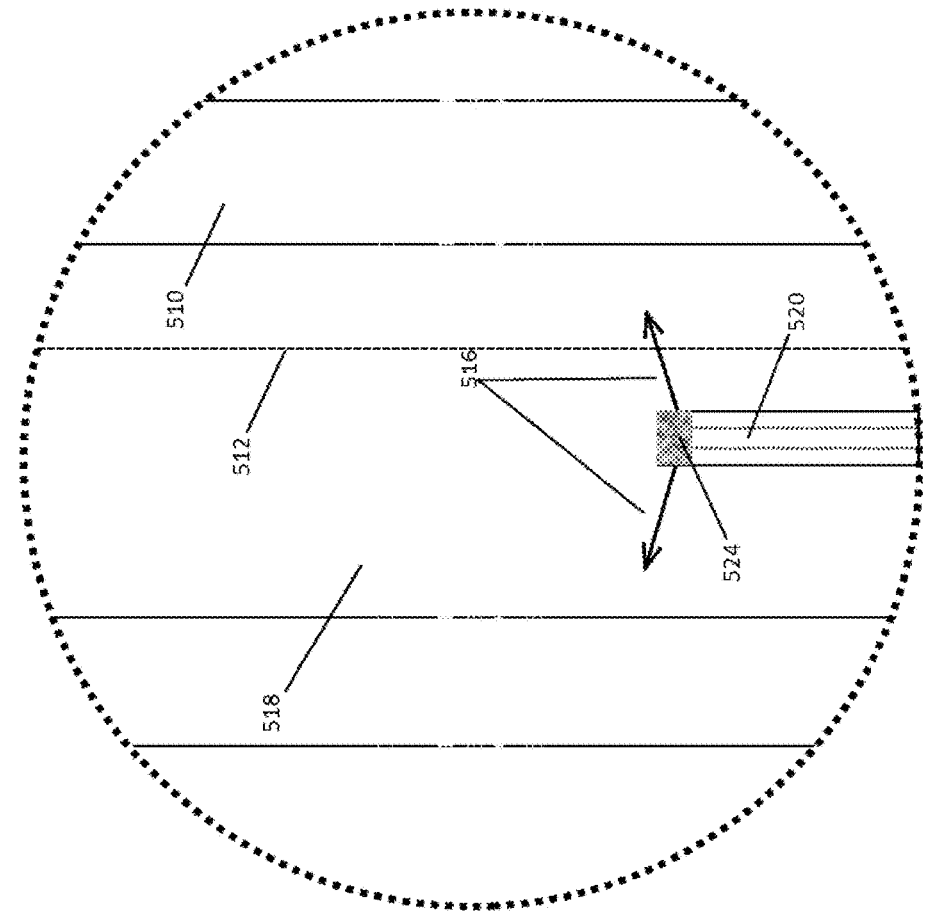
FIG. 5A depicts a cross-section of a portion of a burner assembly according to the present disclosure where the restrictor has a fritted tip.
Figure 5B:
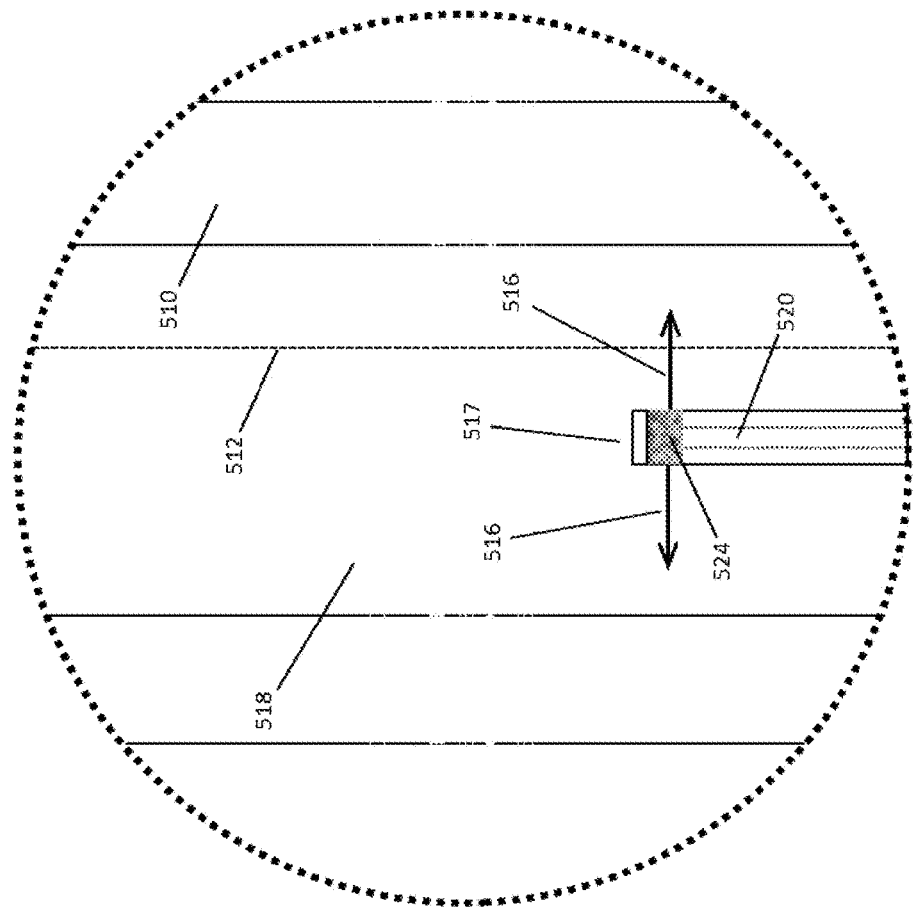
FIG. 5B depicts a cross-section of a portion of a burner assembly according to the present disclosure where the restrictor has a fritted tip, the top of which has been sealed.

Examples of a burner assembly configuration having a "fritted" restrictor is illustrated in FIGS. 5A and 5B. In these examples, the configuration of the burner assembly is identical to that of FIG. 3 except for the adaptation to the second end of the restrictor. Column effluent exits at the fritted second end 524 of restrictor 520 at an angle 516 substantially non-parallel to the longitudinal axis 512 of burner 510. The tip of the fritted second end 524 can be sealed with a cap 517 (FIG. 5B) to force the mobile phase to decompress radially. The mobile phase of the column effluent decompresses and travels through flow path 518 of burner 510 to the flame position.

Figure 6:
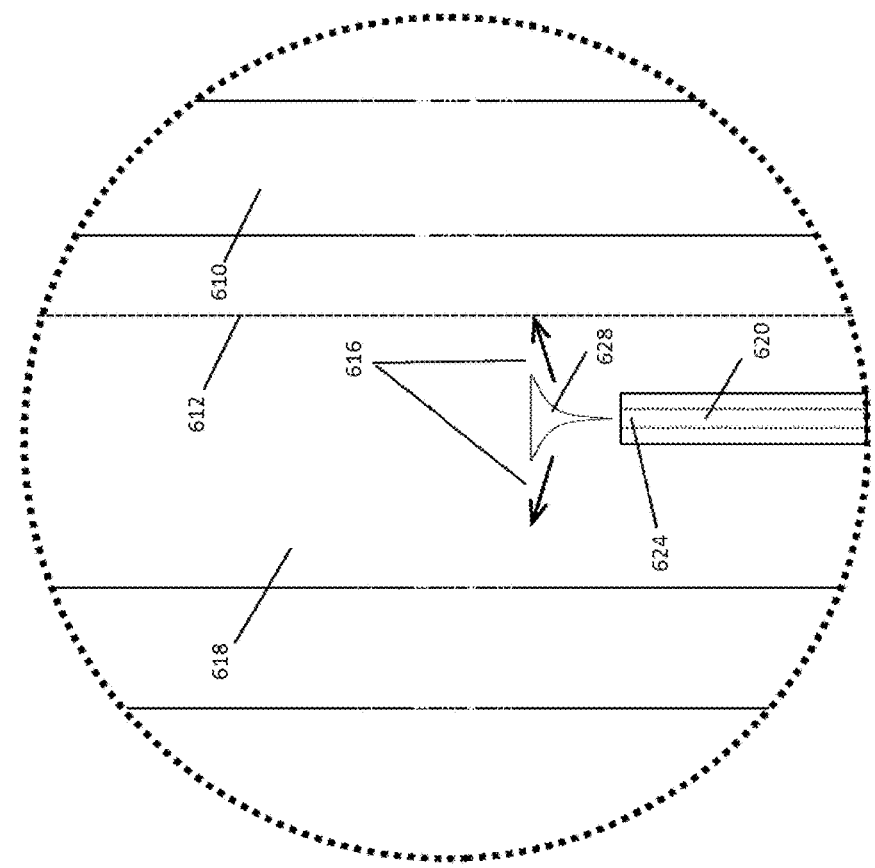
FIG. 6 depicts a cross-section of a portion of a burner assembly according to the present disclosure where the restrictor has a tip comprising a pintle.

An example of a burner assembly configuration having a "pintle" restrictor is illustrated in FIG. 6. In this example, the configuration of the burner assembly is identical to that of FIG. 3 except for the adaptation to the second end of the restrictor. Column effluent exits at the second end 624 of restrictor 620 and is redirected by pintle 628 at an angle 616 substantially non-parallel to the longitudinal axis 612 of burner 610. The mobile phase of the column effluent decompresses and travels through flow path 618 of burner 610 to the flame position.

Figure 7:
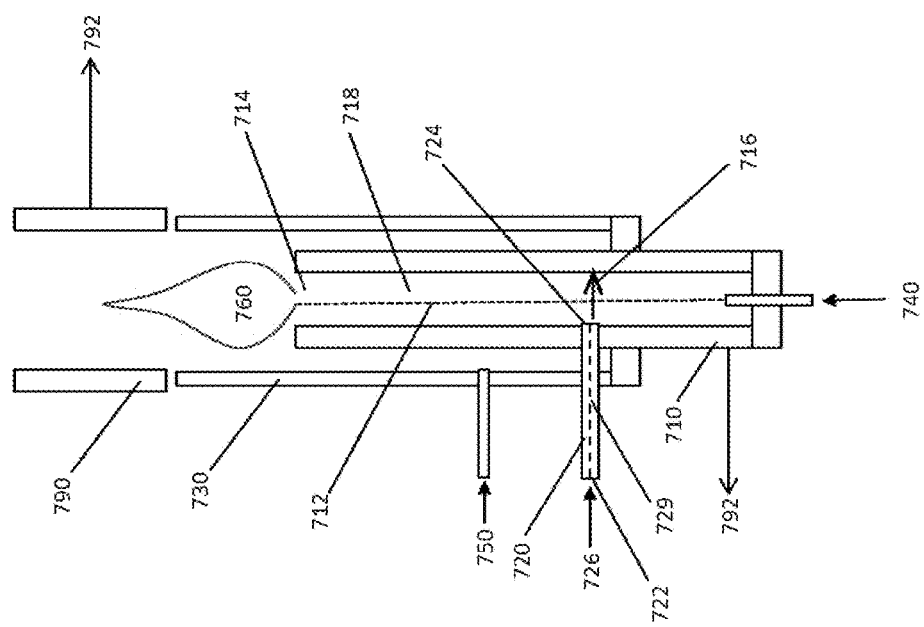
FIG. 7 depicts a cross-section of a burner assembly according to the present disclosure where the restrictor is inserted into a side of the burner.

In another of the above burner assembly configurations, the second end of the restrictor, which has a longitudinal axis, is inserted into the burner such that the restrictor longitudinal axis is substantially non-parallel to the burner longitudinal axis. The restrictor used in such configurations can be a conventional "square cut" restrictor or one of the adapted restrictors described above. In one embodiment, the respective longitudinal axes of the restrictor and the burner are perpendicular. An example of such a burner assembly configuration is illustrated in FIG. 7. The burner assembly comprises a burner 710 and restrictor 720. Longitudinal axis 729 of restrictor 720 is perpendicular to longitudinal axis 712 of burner 710. Burner 710 comprises a burner body having fluid inlets 740 and 750 for receiving combustion gases and a fluid outlet 714 for delivering at least a portion of the combustion gases to flame position 760. Restrictor 720 comprises a first end 722 and a second end 724. Second end 724 of restrictor 720 is located within burner 710. A portion of burner 710 is, in turn, located inside burner housing 730. Column effluent 726 is fed to the FID detector, entering restrictor 720 at its first end 722 and exiting at its second end 724 at an angle 716 substantially non-parallel to the longitudinal axis 712 of burner 720. The mobile phase of the column effluent decompresses and travels through flow path 718 of burner 710 to flame position 760, where one or more separated constituent compositions of the mixture are ionized via combustion. These ions are attracted to collector electrode 790, where they induce a current, which is, in turn, fed to electrometer 792.

In another of the above burner assembly configurations, the burner is adapted so that the at least a portion of the decompressed mobile phase flow stream travels through the flow path in one or more directions substantially non-parallel to the longitudinal axis. This can achieved by using a burner having a tortuous flow path. In one aspect, this tortuous flow path can be formed by packing the flow path of the burner with glass wool. In another aspect, the tortuous flow path can be formed in a burner having one or more members extending from its interior wall surface at an angle substantially non-parallel to its longitudinal axis and which are dimensioned and configured to deflect decompressed mobile phase flow stream in a direction substantially non-parallel to its longitudinal axis. Such members can take the form of a frit or one or more baffles extending from the interior wall of the burner. The members can be porous and/or tapered. The restrictor used in such configurations can be a conventional "square cut" restrictor or one of the adapted restrictors described above.

Figure 8:
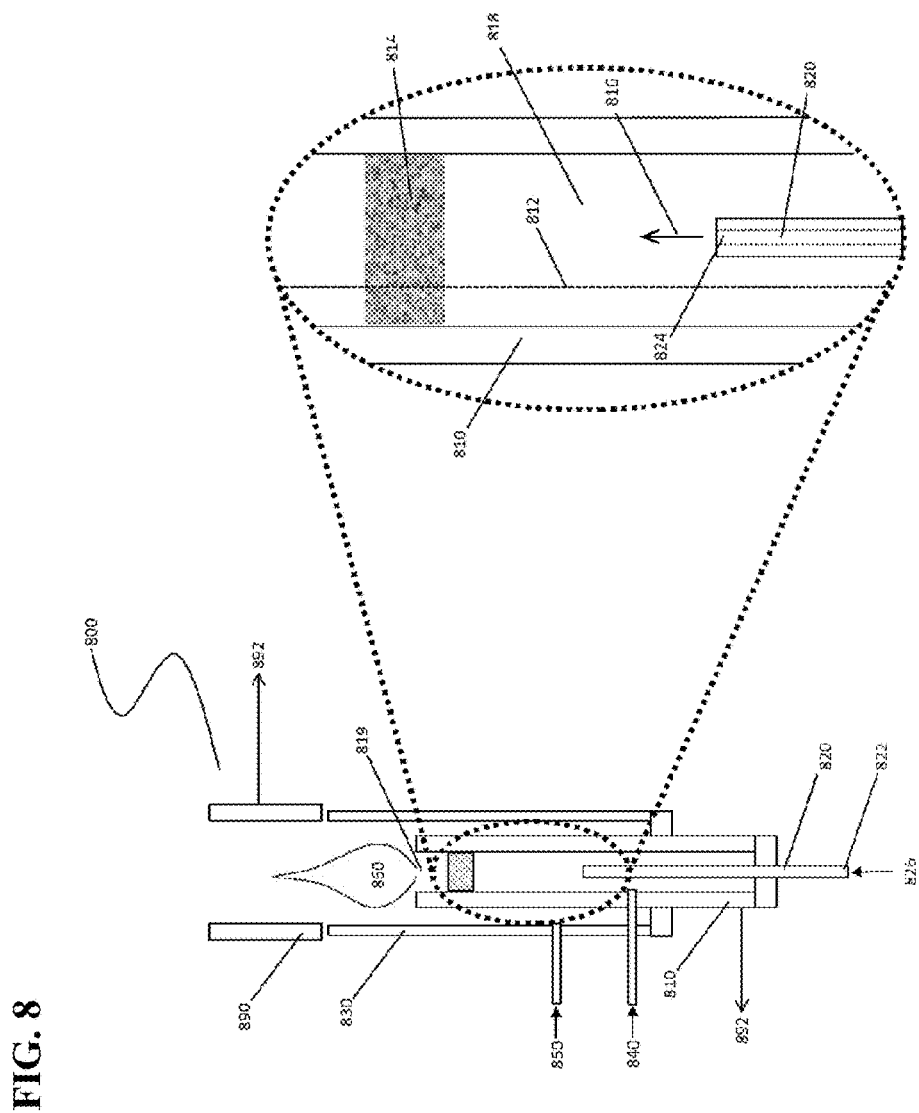
FIG. 8 depicts a cross-section of a burner assembly according to the present disclosure where the flow path of the burner is partially occluded by glass wool or a frit.

An example of such a burner assembly configuration is illustrated in FIG. 8. The burner assembly 800 comprises a burner 810 and restrictor 820. Burner 810 comprises a burner body having fluid inlets 840 and 850 for receiving combustion gases and a fluid outlet 819 for delivering at least a portion of the combustion gases to flame position 860. Restrictor 820 comprises a first end 822 and a second end 824. Second end 824 of restrictor 820 is located within burner 810. A portion of burner 810 is, in turn, located inside burner housing 830. Column effluent 826 is fed to the FID detector, entering restrictor 820 at its first end 822 and exiting at its second end 824 at an angle 816 parallel to the longitudinal axis 812 of burner 810. The mobile phase of the column effluent decompresses and travels through flow path 818 of burner 810 through frit 814. As a result of passing through frit 814, the decompressed mobile phase travels on to flame position 860 at an angle substantially non-parallel to the longitudinal axis 812 of burner 810, where one or more separated constituent compositions of the mixture are ionized via combustion. These ions are attracted to collector electrode 890, where they induce a current, which is, in turn, fed to electrometer 892.

Figure 9:
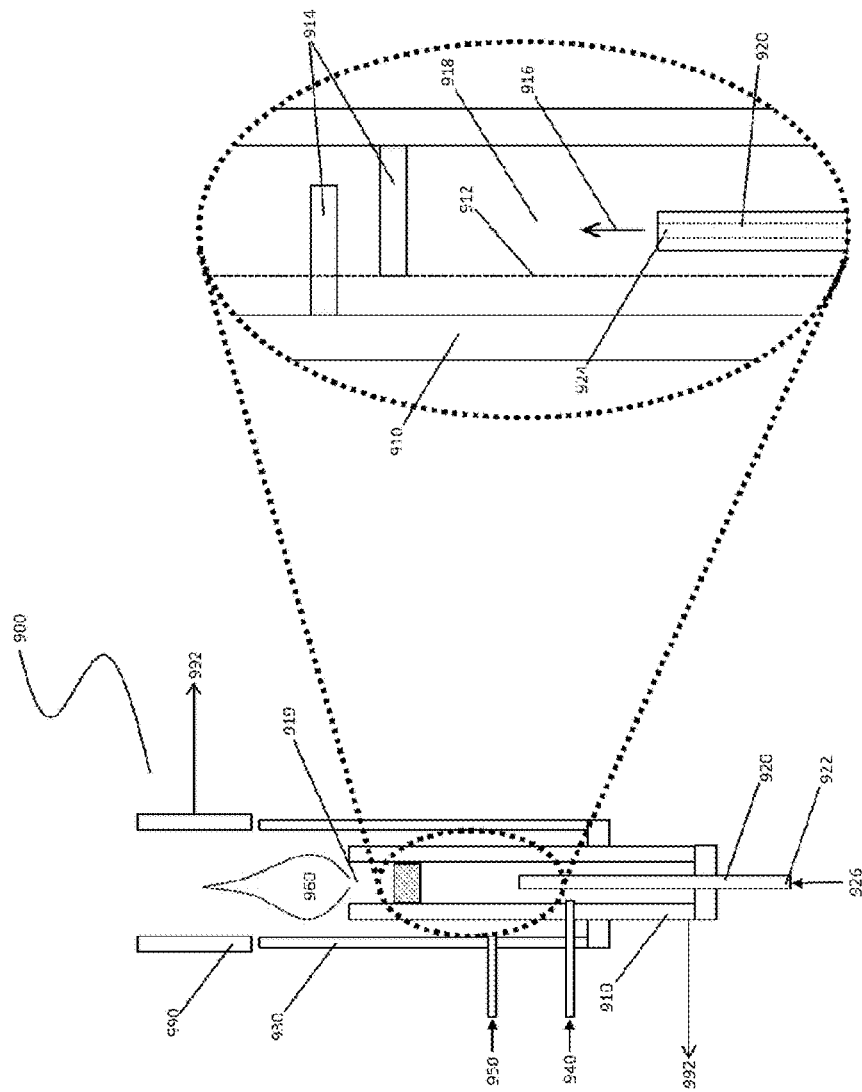
FIG. 9 depicts a cross-section of a burner assembly according to the present disclosure where the flow path of the burner is partially occluded by baffles.

Another example of such a burner assembly configuration is illustrated in FIG. 9. The burner assembly 900 comprises a burner 910 and restrictor 920. Burner 910 comprises a burner body having fluid inlets 940 and 950 for receiving combustion gases and a fluid outlet 919 for delivering at least a portion of the combustion gases to flame position 960. Restrictor 920 comprises a first end 922 and a second end 924. Second end 924 of restrictor 920 is located within burner 910. A portion of burner 910 is, in turn, located inside burner housing 930. Column effluent 926 is fed to the FID detector, entering restrictor 920 at its first end 922 and exiting at its second end 924 at an angle 916 parallel to the longitudinal axis 912 of burner 910. The mobile phase of the column effluent decompresses and travels through flow path 918 of burner 910 past baffles 914. As a result of passing by baffles 914, the decompressed mobile phase travels on to flame position 960 at an angle substantially non-parallel to the longitudinal axis 912 of burner 910, where one or more separated constituent compositions of the mixture are ionized via combustion. These ions are attracted to collector electrode 990, where they induce a current, which is, in turn, fed to electrometer 992.

The present disclosure is also directed to methods of maintaining a flame in a burner assembly of a flame-based detector. These methods comprises the following three steps:
1) providing a burner assembly;
2) passing at least the portion of the mobile phase flow stream through the restrictor at a flow rate of 40 mL/min or greater; and either
3) delivering at least the portion of the mobile phase flow stream into the burner and to the flame position as the decompressed mobile phase flow stream at a force/velocity insufficient to extinguish the flame; or
3') delivering at least the portion of the mobile phase flow stream into the burner and to the flame position as the decompressed mobile phase flow stream such that the decompressed mobile phase flow stream flows to the flame along a non-parallel fluid flow path.

The burner assembly comprises a burner and a restrictor. The burner comprises a burner body having a fluid inlet for receiving combustion gases and a fluid outlet for delivering at least a portion of the combustion gases to a flame position having a flame. The restrictor comprises a restrictor comprising a hollow body comprising a first end for receiving at least a portion of a mobile phase flow stream from a chromatographic system and a second end for delivering the at least a portion of the mobile phase flow stream as a decompressed mobile phase flow stream to the burner. The second end of the restrictor is sized and inserted into the inner burner. The effects of steps 3) and 3') can achieved by employing any of the above-described burner assembly configurations as the burner assemblies of these methods.

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

EXAMPLES

The analytical chromatographic system used was a carbon-dioxide based system (UPC$^2$® System) commercially available from Waters Technologies Corporation, Milford, Mass., USA. The system included an autosampler, a column oven, a 3.0×100 mm ACQUITY UPC² 1.8 µm HSS C18 SB chromatographic column commercially available from Waters Technologies Corporation, Milford, Mass., USA, and an automated back pressure regulator. The mobile phase was 100% carbon dioxide supplied to the system via a fluid delivery module and was maintained at a pressure of 138 bar. The column was heated to a temperature of 45° C. The flow rate was 1.5 mL/min. The sample injection volume was 0.5 µL. At the outlet of the column, and upstream of the backpressure regulator, a "T" fitting directed a portion of the mobile phase flow to the BPR and a portion of the mobile phase flow to a FID (SRI Model 110 FID commercially available from SRI Instruments, Torrance, Calif., USA). The output signal of the FID was analyzed using Empower® 3 Chromatography Data Software commercially available from Waters Technologies Corporation, Milford, Mass., USA.

The measured, decompressed $CO_2$ flow rate directed to the FID was 100 mL/min. At this $CO_2$ flow rate, optimal response was achieved at hydrogen and air flow rates of 97 and 800 mL/min, respectively. The FID body was held at 350° C. The signal to noise ratio of an analyte peak was evaluated over a range of restrictor positions within the FID. A restrictor with a second end angle of decompression of 0 degrees (i.e., "square cut") provided an optimal response when positioned about 15 mm from the tip of the burner. Positions further from or nearer to the burner tip resulted in a decrease in signal to noise. However, when a restrictor with a tip angle of 45 degrees was employed, optimal signal to noise was achieved over the entire range of restrictor position adjustment (i.e., response was independent of restrictor position).

TABLE 1

FID conditions

| Outlet flow (mL/min) | Hydrogen Flow (mL/min) | Air Flow (mL/min) |
|---|---|---|
| 40 | 57 | 560 |
| 100 | 97 | 800 |
| 200 | 202 | 1040 |

TABLE 2

Results Table

| Flow Rate (mL/min) | Decompression angle (°) | | | | | |
|---|---|---|---|---|---|---|
| | 0 | 22 | 45 | 67 | 90 | 135 |
| 40 | X | X | O | O | O | O |
| 100 | X | X | O | ? | N/A | N/A |
| 200 | X | X | O | X | N/A | N/A |

X—response dependent on position
?—response improved but not completely independent of position
O—response independent of position
N/A—no data

What is claimed is:

1. A burner assembly of a flame-based detector comprising:
   (1) a burner comprising a burner body having a fluid inlet for receiving combustion gases and a fluid outlet for delivering combustion gases to a flame position, the burner body defining a flow path extending from the fluid inlet to the flame position and having a longitudinal axis; and
   (2) a restrictor comprising a hollow body comprising a first end for receiving at least a portion of a mobile phase flow stream from a chromatography system and a second end for delivering the at least a portion of the mobile phase flow stream as a decompressed mobile phase flow stream to the burner; and
   wherein during flame-based detection of one or more constituents of the at least a portion of the mobile phase flow stream:
   at least the second end of the restrictor is inserted into the burner; and
   the second end of the restrictor having a tip that is angled to deliver the decompressed mobile phase flow stream to the burner body flow path at an angle substantially non-parallel to the longitudinal axis of the burner.

2. The burner assembly of claim 1, wherein the mobile phase flow stream comprises carbon dioxide.

3. The burner assembly of claim 1, wherein the second end of the restrictor is adapted to deliver the decompressed mobile phase flow stream at an angle of at least 25 degrees with respect to the longitudinal axis of the burner.

4. The burner assembly of claim 1, wherein the second end of the restrictor is adapted to provide radial decompression of the mobile phase.

5. The burner assembly of claim 1, wherein the tip is angled at about 45 degrees.

6. A burner assembly of a flame-based detector comprising:
   (1) a burner comprising a burner body having a fluid inlet for receiving combustion gases and a fluid outlet for delivering combustion gases to a flame position, the burner body having a longitudinal axis and further comprising an interior wall surface defining an inner perimeter of the burner body and one or more members extending from the interior wall surface at an angle substantially non-parallel to the longitudinal axis; and
   (2) a restrictor comprising a hollow body comprising a first end for receiving at least a portion of a mobile phase flow stream from a chromatography system and a second end for delivering the at least a portion of the mobile phase flow stream as a decompressed mobile phase flow stream to the burner;
   wherein during flame-based detection of one or more constituents of the at least portion of the mobile phase flow stream:
   at least the second end of the restrictor is contained within the burner; and
   the one or more members extending from the interior wall are dimensioned and configured to deflect the decompressed mobile phase flow stream in a direction substantially non-parallel to the longitudinal axis.

7. The burner assembly of claim 6, wherein the interior wall surface of the burner defines a tortuous path between the second end of the restrictor and the flame position.

8. The burner assembly of claim 6, wherein the one or more members is a baffle.

9. The burner assembly of claim 6, wherein the one or more members is porous.

10. The burner assembly of claim 6, wherein the one or more members are tapered.

11. A method of maintaining a flame in a burner assembly of a flame-based detector comprising
(1) providing the burner assembly comprising:
  (a) a burner comprising a burner body having a fluid inlet for receiving combustion gases and a fluid outlet for delivering combustion gases to a flame position, the burner body having a longitudinal axis and further comprising an interior wall surface defining an inner perimeter of the burner body and one or more members extending from the interior wall surface at an angle substantially non-parallel to the longitudinal axis; and
  (b) a restrictor comprising a hollow body comprising a first end for receiving at least a portion of a mobile phase flow stream from a chromatography system and a second end for delivering the at least a portion of the mobile phase flow stream as a decompressed mobile phase flow stream to the burner, the second end of the restrictor sized and inserted into the burner
(2) passing at least a portion of the mobile phase flow stream through the restrictor; and
(3) delivering at least the portion of the mobile phase flow stream into the burner and to the flame position as the decompressed mobile phase flow stream such that the decompressed mobile phase flow stream flows to the flame along one or more fluid paths non-parallel to the longitudinal axis.

12. The method of claim 11, wherein the at least a portion of the mobile phase flow stream is passed through the restrictor at a flow rate of 40 mL/min or greater.

* * * * *